United States Patent
Chen et al.

(10) Patent No.: US 6,716,405 B1
(45) Date of Patent: Apr. 6, 2004

(54) PROCESS FOR REMOVING UNREACTED AMMONIA FROM AN EFFLUENT IN A HYDROCARBON AMMOXIDATION REACTION

(75) Inventors: Xin Chen, Shanghai (CN); Linghua Wu, Shanghai (CN)

(73) Assignees: China Petro-Chemical Corporation, Beijing (CN); Shanghai Research Institute of Petrochemical Technology, SINOPEC, Shanghai (CN)

( * ) Notice: Subject to any disclaimer, the term of this patent is extended or adjusted under 35 U.S.C. 154(b) by 0 days.

(21) Appl. No.: 09/440,277

(22) Filed: Nov. 15, 1999

Related U.S. Application Data

(62) Division of application No. 09/090,918, filed on Jun. 5, 1998, now abandoned.

(30) Foreign Application Priority Data

Jun. 6, 1997 (CN) .......................................... 97106455 A

(51) Int. Cl.⁷ ........................... C01C 1/12; C07C 253/24
(52) U.S. Cl. ...................... 423/237; 423/375; 423/376
(58) Field of Search .............................. 423/238, 375, 423/376, 237; 558/319, 320

(56) References Cited

U.S. PATENT DOCUMENTS

| | | | |
|---|---|---|---|
| 2,581,134 A | 1/1952 | Odell .......................... | 422/139 |
| 2,606,104 A | 8/1952 | Hogan et al. ................ | 422/139 |
| 2,777,760 A | 1/1957 | Dineen et al. ............... | 422/139 |
| 3,230,246 A | 1/1966 | Callahan et al. .......... | 260/465.3 |
| 3,427,343 A | 2/1969 | Callahan et al. .......... | 260/465.3 |
| 3,644,472 A | 2/1972 | Paleologo et al. ........ | 260/465.3 |
| 3,784,561 A | 1/1974 | Slinko et al. ............. | 260/465.3 |
| 3,944,592 A | 3/1976 | Sheely ...................... | 260/465.3 |
| 4,470,931 A * | 9/1984 | Callahan et al. .......... | 260/465.3 |
| 4,622,424 A | 11/1986 | Callahan et al. ............. | 562/545 |
| 5,453,254 A | 9/1995 | Lefers et al. ................ | 422/139 |

FOREIGN PATENT DOCUMENTS

| | | | | |
|---|---|---|---|---|
| CN | 1021638 | | 10/1991 | ............ B01J/23/84 |
| CN | 1172693 A | | 2/1998 | .......... B01J/27/138 |
| JP | 8-27087 | | 1/1996 | .......... C07C/255/07 |
| WO | WO 96/23766 | | 8/1996 | .......... C07C/255/08 |
| WO | WO 96/25391 | | 8/1996 | .......... C07C/253/26 |

* cited by examiner

Primary Examiner—Stanley S. Silverman
Assistant Examiner—Maribel Medina
(74) Attorney, Agent, or Firm—Jones Day

(57) ABSTRACT

A process for removing unreacted ammonia from an effluent of a catalyst bed used in a hydrocarbon ammoxidation reaction is provided. The process includes a step of providing a fluidized bed reactor. The reactor includes the catalyst bed for reacting ammonia and hydrocarbons therein. The reactor also includes a dilute phase of the catalyst bed disposed above the catalyst bed. The reactor further includes a set of internals disposed at least partially within the dilute phase of the catalyst bed. The reactor additionally includes an inlet of a first-stage cyclone separator disposed above the set of internals. The process also includes a step of removing the unreacted ammonia from the effluent of the catalyst bed by passing the effluent through the set of internals. The ammonia and hydrocarbons present in the effluent contact the dilute phase of the catalyst bed and react therein.

5 Claims, No Drawings

PROCESS FOR REMOVING UNREACTED AMMONIA FROM AN EFFLUENT IN A HYDROCARBON AMMOXIDATION REACTION

This application is a divisional of application Ser. No. 09/090,918, filed Jun. 5, 1998 abandoned.

This invention relates to a fluidized bed reactor for ammoxidation of hydrocarbons and, more particularly, to a fluidized bed reactor with internals installed in proximity to upper region of the catalyst bed, capable of enhancing the contact efficiency between gas and solid phases.

It is an important subject in petrochemical industry to produce unsatured nitrites by ammoxidation process from hydrocarbons, among which the ammoxidation of propylene and isobutene has long been commercialized for the manufacture of acrylonitrile and methyl acrylonitrile, respectively, and the ammoxidation of paraffinic hydrocarbons has also been under development. A common problem associated with these reactions is due to the fact that unsaturated nitrites are usually unstable and liable to polymerization under basic conditions. For any ammoxidations therefore, it is necessary to eliminate the unreacted ammonia from the product gases. To remove the unreacted ammonia, the prior art has employs a method by sulfuric acid quenching. This method will produce large quantities of nitrile-containing ammonium sulfate waste water, which is difficult to dispose. The strict legislation imposed on pollutant emissions in most countries has rendered the disposal of ammonium sulfate byproduct a critical issue.

Taking the ammoxidation of propylene to acrylonitrile for example, propylene, upon passing through a fluidized bed reactor together with ammonia and air, is ammonia oxidized to form a major product of acrylonitrile and a number of byproducts including acetonitrile, hydrogen cyanide, acrolein, acrylic acid, carbon monooxide and carbon dioxide, as well as small amounts of unreacted propylene and ammonia. After exiting the reactor, the gaseous effluent is cooled and then enters a neutralizing column, where the unreacted ammonia is absorbed by aqueous sulfuric acid to produce ammonium sulfate. At the same time, parts of water vapor are also condensed out, thereby causing the formation of ammonium sulfate waste water. After removing the unreacted ammonia, the gas is introduced into an absorber, where all the organic compounds are absorbed from the gas by low-temperature water. The absorption liquid is then sent to an acrylonitrile recovery and refining unit for the separation of high purity of acrylonitrile, hydrogen cyanide and acetonitrile.

In the above described process of acrylonitrile production, it is very important to remove unreacted ammonia with sulfuric acid from the effluent gas in the neutralizing column, because both acrylonitrile and hydrogen cyanide are substances liable to polymerization, especially in neutral and slightly alkaline conditions. Not only will this cause product loss of acrylonitrile and hydrogen cyanide, but contaminate the equipment and produce ammonium sulfate waste water.

The composition of ammonium sulfate waste water is complex, approximately comprising the following groups:

1. polymers: Because pH value of the circulating spray liquid in the neutralizing column is controlled within the range of 2–7, certain amount of products, such as acrylonitrile, hydrogen cyanide and acrolein, may polymerize to form high polymers. Losses caused by polymerization, calculated based on the total amount of their formation are: acrylonitrile 2–5%, hydrogen cyanide 3–8%, and acrolein up to 40–80%. Therefore the polymer content in the ammonium sulfate waste water is very high. A wider molecular weight distribution is another characteristics of polymers present in the waste water, i.e. some polymers with low molecular weight are soluble in the ammonium sulfate waste water, but other polymers with higher molecular weight will form black solid insoluble in water, thereby leading difficulty in recovering ammonium sulfate.
2. high boiling components: Since the operation temperature within the neutralizing column is about 80° C., acrylic acid will be condensed from the effluent gas and present in the ammonium sulfate waste water. Another high boiling component is cyanhydrin, which is formed by the condensation between carbonyl compounds and hydrogen cyanide.
3. low boiling components: mainly acrylonitrile, acetonitrile and hydrogen cyanide etc. dissolved in the ammonium sulfate waste water, their content being normally in the range of 500–5000 ppm, depending on the temperature of spray liquid.
4. catalyst fine particles: During the production of acrylonitrile in fluidized bed reactor, the major part of catalyst fine particles entrained from the catalyst bed by the product gas is recovered by cyclones and circulated back to the bed. However, small amount of catalyst fines will be blown out of the reactor by the effluent gas and then scrubbed down in the neutralizing column. The catalyst blow-off quantity is about 0.2.–0.7 kg per ton of acrylonitrile produced.

Accordingly, it is very difficult to recover crystalline ammonium sulfate from the ammonium sulfate waste water. Simply burning off the effluents without a prior recovery of ammonium sulfate therefrom will cause secondary pollution owing to the formation of sulfur dioxide, which is not allowed to discharge directly to the atmosphere in most countries. Another problem associated with the disposal of ammonium sulfate waste water by burning method is a combustion temperature as high as 850–1100° C. required to burn out the cyanides from the waste water, thus causing large quantities of fuel consumption. Since sulfur dioxide contained in the combustion flue gas is corrosive to steel material the use of waste heat boilers for recovering the heat energy is limited. Moreover, direct vent of high temperature flue gas will cause thermal pollution to the atmospheric environment.

In summary, the formation of ammonium sulfate in the production of acrylonitrile leads to a severe problem, which has severely limited further development of the acrylonitrile manufacture industry. Therefore development of a clean process for the production of acrylonitrile which produce no ammonium sulfate has become the concerned focus in the art worldwide. The key point of this clean process is to maximize ammonia conversion during the production in order to elate the unreacted ammonia Elimination of unreacted ammonia can be achieved by two ways: one starts with the catalyst to increase ammonia conversion of the catalyst; the other starts with the ammoxidation reaction to enable ammoxidation of propylene and elimination of unreacted ammonia to proceed separately.

Further increasing ammonia conversion of the propylene ammoxidation catalyst can be difficult to achieve. To take account of ammoxidation only, the catalyst is required to have lower ability to decompose ammonia, i.e. to yield higher acrylonitrile yield while using a lower feed ratio of propylene to ammonia. If the catalyst has a higher decomposition ability for ammonia, the increase of ammonia consumption will render it uneconomic. Therefore these two requirements are contradictory. Since ammonia conversion of the current catalyst is very low, to increase ammonia conversion of the catalyst to certain level without increasing the ammonia consumption still deserves attention. Because certain amount of acrylic acid is also formed during propylene ammoxidation, it is not necessary to increase ammonia conversion of the catalyst to as high as 100%. For a conversion up to 97–98%, it may not need essentially to add sulfuric acid for neutralization. For example, Chinese Patent 96116456.5 is an example in an effort to increase ammonia conversion of the catalyst. From the viewpoint of extended stable operation of the plant, the inventor believes that there should be other measures to attain complete elimination of the unreacted ammonia. This is because of the fact that the ability of a catalyst to decompose ammonia is related to how long it has been used, and also influenced by the operating conditions of the reactor, which cannot be maintained unchanged for long periods of time.

To eliminate the unreacted ammonia by virtue of the secondary reaction of propylene ammoxidation is a useful method and has been disclosed in patents. U.S. Pat. Nos. 5,457,223 and 5,466,857, Japanese Patent No. 96-27087 and WO 9625391 disclose that methanol, acetonitrile and other oxidable organic compounds, introduced into the dilute phase at the upper region of a fluidized bed reactor where propylene is ammonia-oxidized with molybdenum-bismuth-iron system catalyst to synthesize acrylonitrile, may react with ammonia therein to form hydrogen cyanide and eliminate ammonia. At the optimum conditions, ammonia can be reacted completely. This method, however, suffers from the oxygen depletion problem at the dilute phase of the reactor where oxygen is needed for ammonia to react with organic compounds, and the catalyst will therefore be over-reduced. As a result, the single-pass yield of acrylonitrile will decrease, and the catalyst stability may be affected as well.

WO 9623766 discloses another method by adjusting the molar ratio of the feed to the reactor to keep the molar ratio of the organic acids formed such as acrylic acid etc. to the unreacted ammonia in the range of 0.8–3.0. In this case, the unreacted ammonia will subsequently combine with the organic acids to form the corresponding ammonium salts, thereby eliminating the need of sulfuric acid. The disadvantage of this method is the formation of unsaturated carbonyl compounds in large amounts along with the formation of organic acids. This will cause difficulty for the recovery and refining of acrylonitrile, as well as decease its single-pass yield.

The inventor has identified, through a consistent and thorough review of the full range of fundamental processes in acrylonitrile synthesis at a fluidized bed reactor, that the unreacted ammonia may be eliminated by resorting the secondary reaction of propylene ammoxidation, even without the addition of any oxidable organic compounds.

To overcome these and other deficiencies of the prior art it is therefore an object of the present invention to provide a fluidized bed reactor for ammoxidation of hydrocarbons, which contains a set of suitable internals installed in proximity to the upper region of the catalyst bed, capable of enhancing the contact efficiency between gases and solids therein, and serves the function of increasing the ammonia conversion, thereby decreasing the content of unreacted ammonia in the effluent gas.

The above mentioned internals include packings, baffles and screens etc. Said internals help to bring about more uniform mixing between the reactive gas leaving the catalyst bed and the catalyst entrained by the gas flow in the space above the catalyst bed, thus increasing the contact efficiency between gas and catalyst particles, which will be beneficial to the further reaction occurring within the dilute phase zone and elimination of the unreacted ammonia from the effluent gas.

Within the reactor the internals are positioned, for baffles or screens, with their bottom plate (screen) beneath the surface of the catalyst to keep its depth not beyond 20% of the height of the fluidized bed, while with their top side not beyond the inlet of the first-stage cyclone separator, preferably at the level of the dust hopper of the cyclone separator. For packings, the positions of their top and bottom side within the reactor are the same as said above.

The packings used are made of screens generally limited to 10 mesh or more, in the form of circular, cylindrical, square, rectangular, honeycomb and the like, and with a void factor (fractional free area) in the range of 20–80%, preferably in the range of 35–60%. The packings may be packed within the reactor either randomly or regularly. Special method can also be used, for example, to fix the packings by springs so as to enable it to vibrate under the action of product gas flow to prevent their surfaces from catalyst deposition The baffles or screens used include perforated grid plates, perforated plates, perforated plates with cone or pyramid cap or louver plates etc. Their openings may have different geometries, such as rectangular, triangular, circular, elliptical etc. with a void factor (fractional free area) in the range of 20–80%, preferably in the range of 35–65%. The baffles or screens may be placed horizontally or at a certain slope. For inclined arrangement, the slope angle must be greater than the angle of repose of the catalyst to prevent catalyst accumulation over its surface. The spacing L between various layers of baffles or screens may be identical or different, depending on the inside diameter of the reactor (D). L/D may vary from 0.2 to 2.0.

At the upper region of the catalyst bed of the fluidized bed reactor ammonia undergoes secondary reaction, accompanied by heat generation. Accordingly, the ammonia conversion of the catalyst should not be too low, to prevent temperature at the reactor top from going too high. In this invention, the ammonia conversion is required above 85%, preferably above 93%. All olefin ammoxidation catalysts, more preferably catalysts with molybdenum oxide as the major component are applicable to this invention, such as the catalyst described in Chinese Patent CN1021638C. A catalyst of higher ammonia conversion is more preferred.

Gas superficial velocity within the fluidized bed reactor bears a relation to the catalyst concentration at the dilute phase of the reactor top. It should be in the range of 0.5–0.8 m/s, preferably in the range of 0.6–0.75 m/s. The temperature at the upper reactor should be the same as or close to the temperature of catalyst bed. The reaction pressure depends on the activity of the catalyst used, normally in the range of 0.05–0.2 MPa.

This invention is the main part of an overall acrylonitrile manufacture process which can minimize ammonium sulfate formation or produce no ammonium sulfate. After propylene, ammonia and air pass through the fluidized bed reactor of the invention, the product gas is cooled and enters a quenching column for further cooling, then is sent into a scrubber, where all organic matters are absorbed from the gas by low-temperature water. The absorption liquid is passed to an extraction column, where water is used as a solvent to separate acrylonitrile from acetonitrile. Raw acrylonitrile overhead out of the column contains hydrogen cyanide and small amount of water. It then passes through a column to remove hydrogen cyanide and a dewatering column, thereby obtaining acrylonitrile product of high purity.

The present invention uses the secondary reaction taking place within the dilute phase of the fluidized bed reactor to remove unreacted ammonia from the product gas, but it adds no organic compounds at all. The effluent gas leaving the catalyst bed contains, in addition of acrylonitrile and byproducts such as acetonitrile, hydrogen cyanide, acrolein, acrylic acid, carbon monoxide, carbon dioxide etc., small amount of unreacted propylene and ammonia, which contact with the catalyst present at the dilute phase of the fluidized bed for further reaction. The unreacted ammonia reacts with acrolein byproduct and residual propylene to form acrylonitrile, thereby increasing the acrylonitrile production and decreasing the acrolein content. It therefore has an advantage.

Since the effluent gas leaving the catalyst bed does not rise uniformly, and the internals installed at the dilute phase of the fluidized bed are available to bring about more uniform mixing between the gas and the catalyst and increase the contact efficiency therebetween, the ammonia conversion is thus increased to enable the content of unreacted ammonia to be decreased and good results to achieve. The fluidized bed reactor of this invention is applicable to the ammoxidation of propane, propylene, isobutene and xylene, not only for the retrofitting of existing facilities, but for the developing of new processes. For ammoxidation process, this invention can intensify productivity, increase reaction efficiency, simplify the process flowsheet, decrease pollution to the environment, and thus yield greater economy. The invention will be further illustrated by the following examples.

COMPARATIVE EXAMPLE 1

A catalyst of the same composition as in Example 1 of CN 102163C was used. The fluidized bed reactor was 38 mm in inside diameter and about 2 m tall. 550 g of catalyst were added with a catalyst bed height of 320 mm. The reaction temperature was 435° C., reaction pressure 0.08 MPa, the feed ratio was propylene:ammonia:air=1:1.2:9.8, and the feed rate of the gas mixture was 4.3 L/min. The reaction result indicated a propylene conversion of 96.2%, acrylonitrile single-pass yield of 80.1%, acrylonitrile selectivity of 83.3%, and ammonia conversion of 93%.

Example 1

The same condition was followed as in Comparative Example 1, except that 5 perforated plates were placed at the reactor top with the height of the first plate from the gas distributor as 300 mm, and the heights of other four plates as 350, 400, 450 and 500 mm, respectively. The holes were 4 mm in diameter and the fraction of plate consisting of free area was 40%. The reaction result showed a propylene conversion of 98.5%, acrylonitrile single-pass yield of 81.7%, acrylonitrile selectivity of 82.9%, and ammonia conversion of 96.2%.

Example 2

The same condition was used as in Example 1 except that 3 identical perforated plates were placed with the first plate at the same height as in Example 1 and the heights of the $2^{nd}$ and $3^{rd}$ plates as 400 and 500 mm, respectively. The reaction result showed a propylene conversion of 97.8%, acrylonitrile single-pass yield of 81.2%, acrylonitrile selectivity of 83.0%, and ammonia conversion of 95.5%.

Example 3

The same condition was used as in Example 1 except that 8 identical perforated plates were placed with the first plate at the same height as in Example 1 and a plate spacing of 30 mm. The reaction result showed a propylene conversion of 98.8%, acrylonitrile single-pass yield of 81.7%, acrylonitrile selectivity of 82.7%, and ammonia conversion of 96.5%.

Example 4

The same condition was used as in Example 2 (i.e. adding 3 perforated plates) except that the catalyst amount was 750 g and the feed rate of gas mixture was increased to 6 L/min. The reaction result showed a propylene conversion of 98.7%, acrylonitrile single-pass yield of 81.8%, acrylonitrile selectivity of 82.9%, and ammonia conversion of 97.5%.

Example 5

The same condition was used as in Example 1 except that within the reactor were placed cylindrical packings made of 10 mesh×6 mm stainless steel screens. The height of packings bottom from the gas distributor was 300 mm and its length 200 mm. The reaction result showed a propylene conversion of 98.8, acrylonitrile single-pass yield of 81.4%, acrylonitrile selectivity of 82.4%, and ammonia conversion of 97.2%.

It can be seen from the Example mentioned above:
1. For the fluidized bed reactor with the internals comprising packings or baffles according to the invention, the ammonia conversion is increased by 4–5% with acrylonitrile single-pass yield and acrylonitrile selectivity keeping fixed.
2. Increasing the number of baffles (screens) or the height of packings as well as properly raising the feed rate of the gas result in better ammonia conversion.

What is claimed is:
1. A process for removing unreacted ammonia from an effluent of a catalyst bed used in ammoxidation of hydrocarbons, comprising the steps of:
   (a) providing a fluidized bed reactor, said reactor comprising:
      (1) a fluidized catalyst bed for reacting ammonia and hydrocarbons therein;
      (2) a dilute phase of the catalyst bed disposed above the fluidized catalyst bed;
      (3) a set of internals introduced into space above the fluidized catalyst bed layer and disposed at least partially within the dilute phase of the fluidized catalyst bed;
      (4) an inlet of a first-stage cyclone separator disposed above the set of internals, wherein the fluidized bed reactor does not comprise a fixed catalyst bed; and
   (b) removing the unreacted ammonia from the effluent of the fluidized catalyst bed by passing the effluent through the set of internals, wherein the ammonia and hydrocarbons present in the effluent contact the dilute phase of the catalyst bed and react herein.
2. The process according to claim 1, wherein the set of internals are selected from the group consisting of packing, baffles, screens and combinations thereof.
3. The process according to claim 1, wherein a bottom side of the set of internals is at a depth within the catalyst bed of not greater than 20% of the total height of the catalyst bed.
4. The process according to claim 1, wherein the hydrocarbons are of a compound selected from the group consisting of propane, propylene, isobutene, xylene and combinations thereof.

5. A process for removing unreacted ammonia from an effluent of a catalyst bed used in ammoxidation of hydrocarbons, comprising the steps of:
- (a) providing a fluidized bed reactor, said reactor comprising:
  - (1) a fluidized catalyst bed for reacting ammonia and hydrocarbons therein;
  - (2) a dilute phase of the catalyst bed disposed above the fluidized catalyst bed;
  - (3) a set of internals introduced into space above the fluidized catalyst bed layer and disposed at least partially within the dilute phase of the fluidized catalyst bed, wherein the fluidized bed reactor does not comprise a fixed catalyst bed; and
- (b) removing the unreacted ammonia from the effluent of the fluidized catalyst bed by passing the effluent through the set of internals, wherein the ammonia and hydrocarbons present in the effluent contact the dilute phase of the fluidized catalyst bed and react therein.

* * * * *